United States Patent [19]

Hosonuma et al.

[11] Patent Number: 5,049,742
[45] Date of Patent: Sep. 17, 1991

[54] APPARATUS FOR DETECTING DETERIORATION OF ENGINE OIL

[75] Inventors: Kunihiko Hosonuma; Yasushi Naito; Ryoichi Inada, all of Toda, Japan

[73] Assignee: Kyodo Oil Technical Research Co., Ltd., Tokyo, Japan

[21] Appl. No.: 437,519

[22] Filed: Nov. 16, 1989

[51] Int. Cl.⁵ ............................................. G01N 21/35
[52] U.S. Cl. .................................... 250/301; 250/343; 356/70
[58] Field of Search ................... 250/343, 301; 356/70, 356/246

[56] References Cited

U.S. PATENT DOCUMENTS 3,526,127  9/1970  Sarkis ................................. 250/343
3,777,283  12/1973 Elkins ................................. 356/246
4,570,069  2/1986  Gager ................................. 250/343
4,628,204  12/1986 Maes .................................. 356/70

FOREIGN PATENT DOCUMENTS 209693  5/1984  Fed. Rep. of Germany ...... 356/246
236048  11/1985 Japan ................................. 356/70
266342  11/1988 Japan ................................. 356/70

Primary Examiner—Carolyn E. Fields
Attorney, Agent, or Firm—Oliff & Berridge

[57] ABSTRACT

An apparatus for detecting the deterioration of an engine oil including a ceramic heater radiating infrared light including infrared radiation having a wavelength of 6.1 micron meters which is equal to the specific infrared absorption peak of ester of nitric acid contained in the engine oil. The infrared light is made incident upon a photodetector via a band pass filter having a center wavelength of 6.1 micron meters to detect an amount of the ester of nitric acid contained in the engine oil. It has been experimentally confirmed that an amount of the ester of nitric acid is proportional to the total acid value which is a measure of the deterioration of the engine oil, so that by suitably processing an output signal of the photodetector, it is possible to detect the deterioration of the engine oil. The thus detected deterioration may be displayed on a display device provided on a front pedal of a car.

19 Claims, 12 Drawing Sheets

FIG._2a
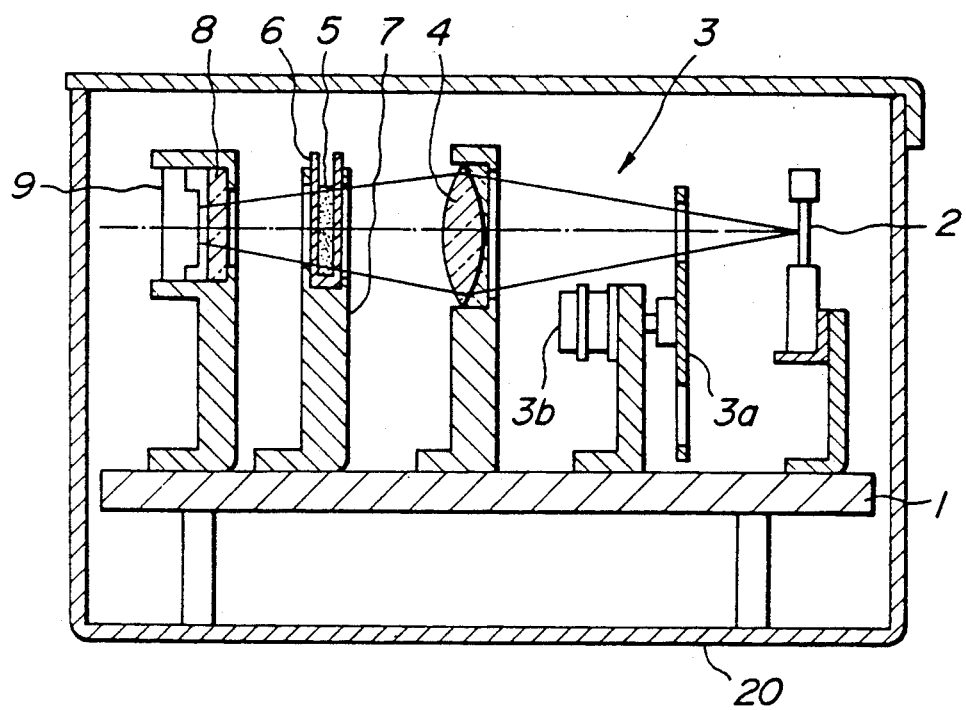
FIG._2b
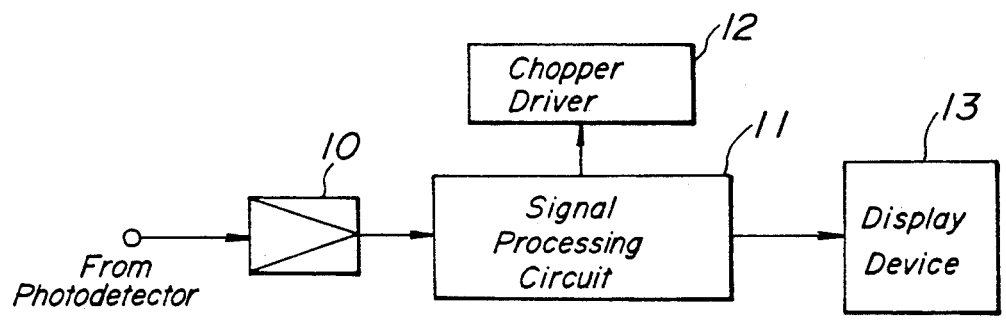

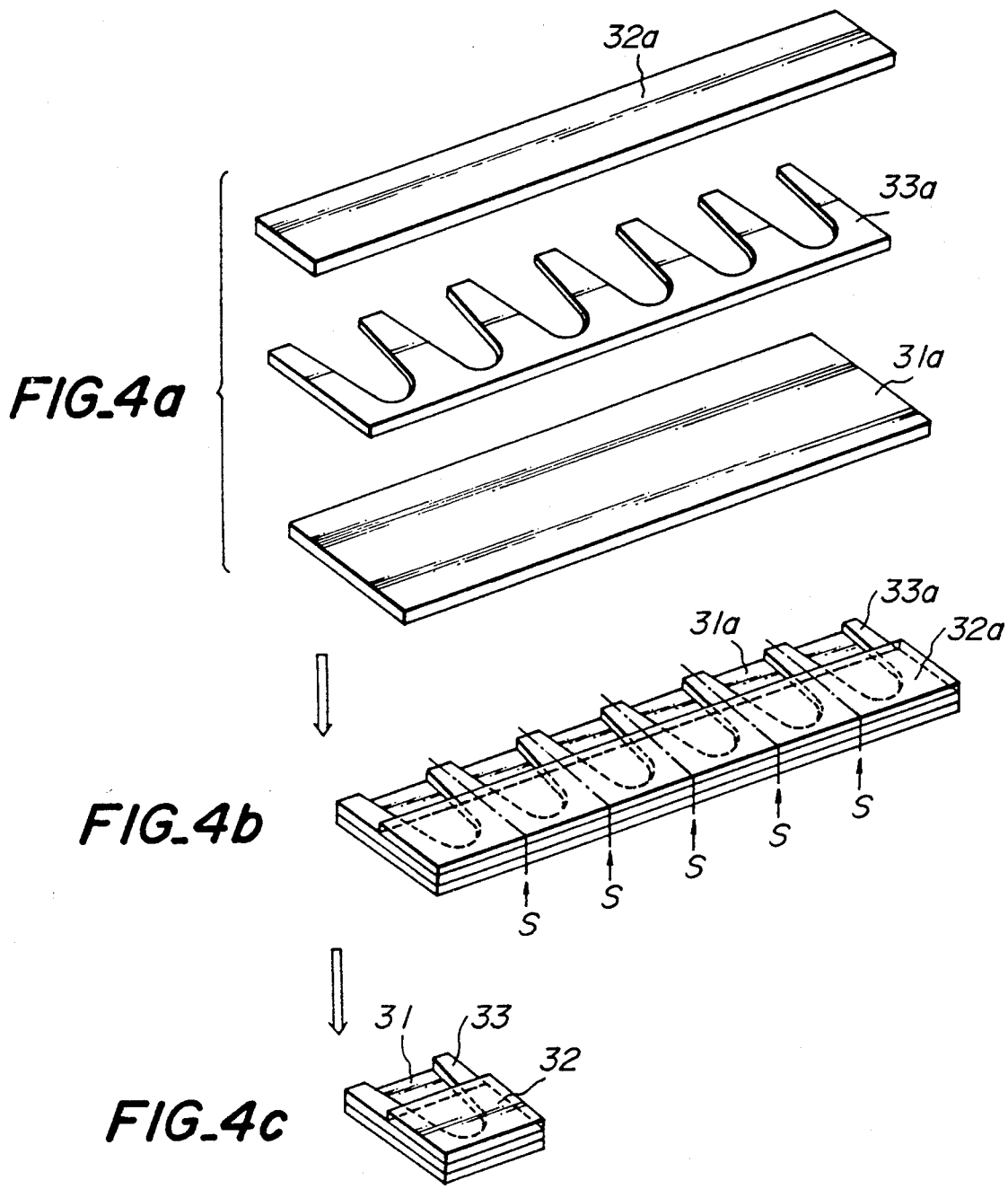

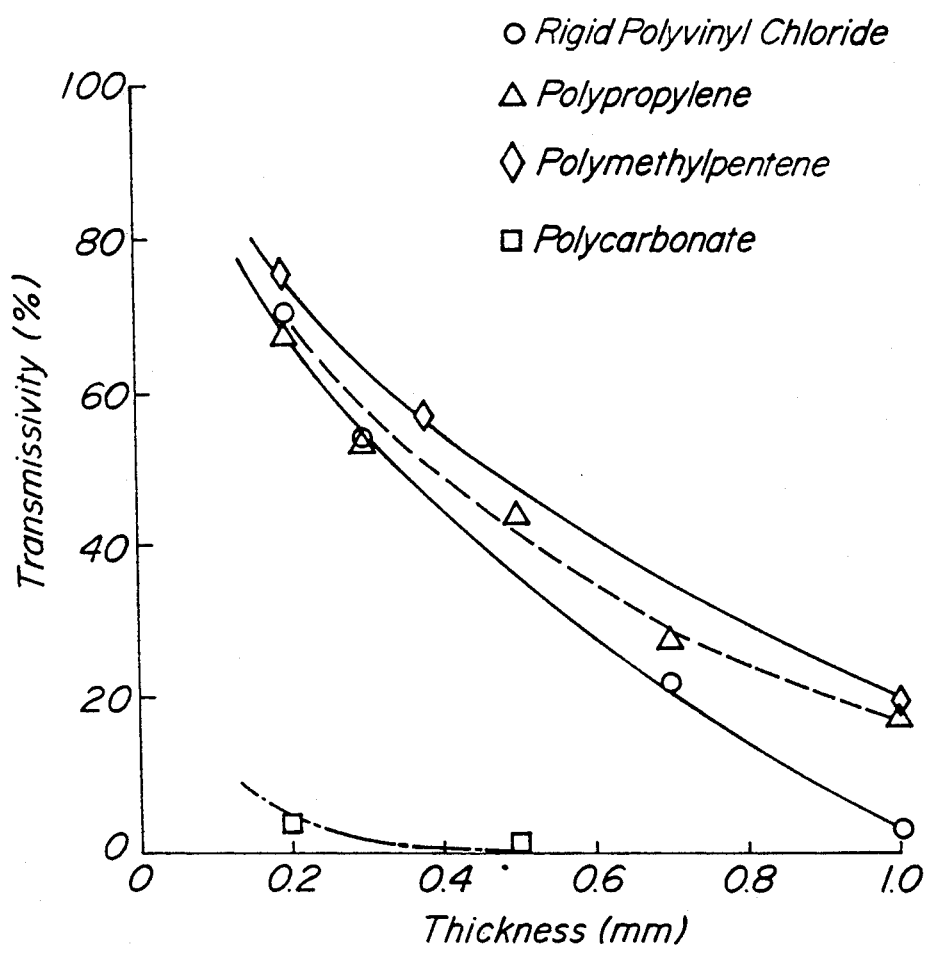
FIG_5

FIG_6a
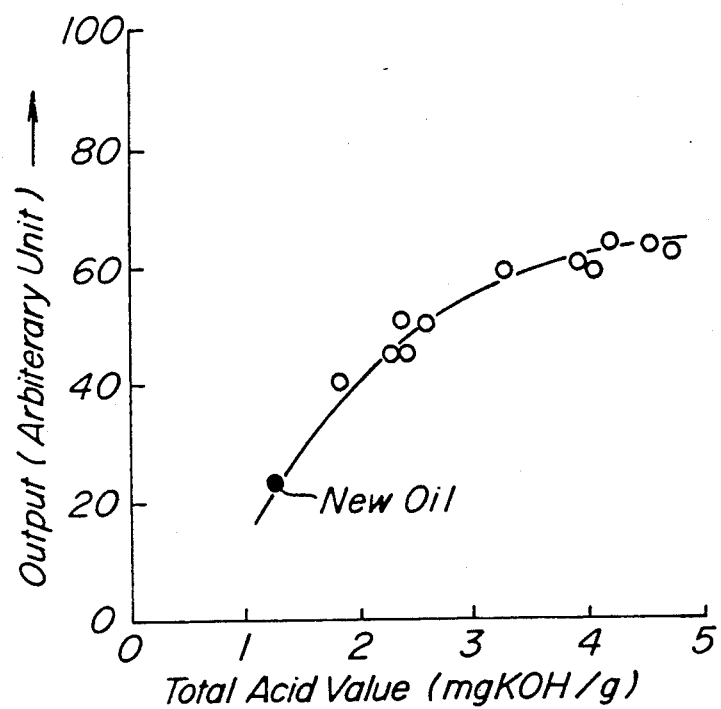
FIG_6b
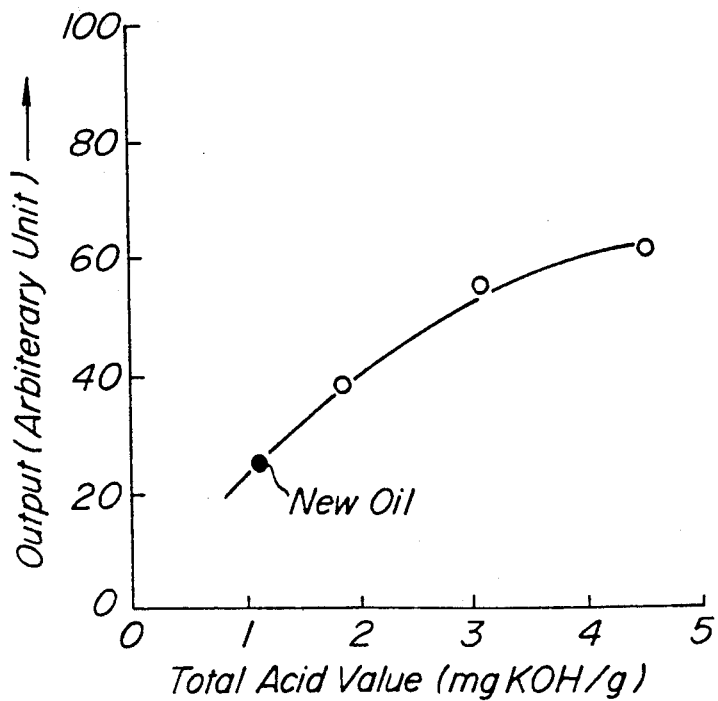

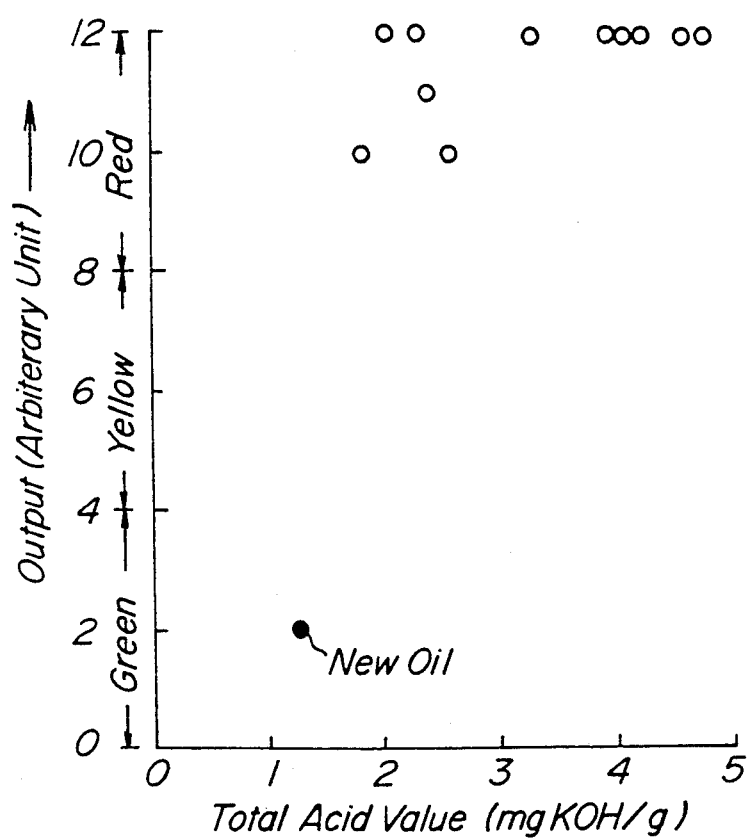
FIG_6c

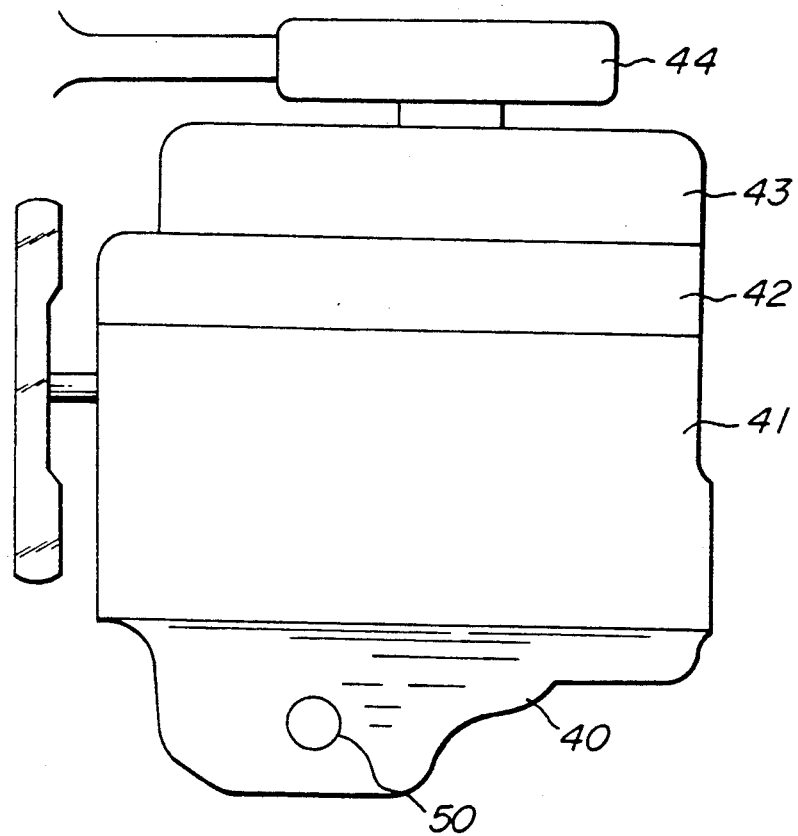
FIG_7a

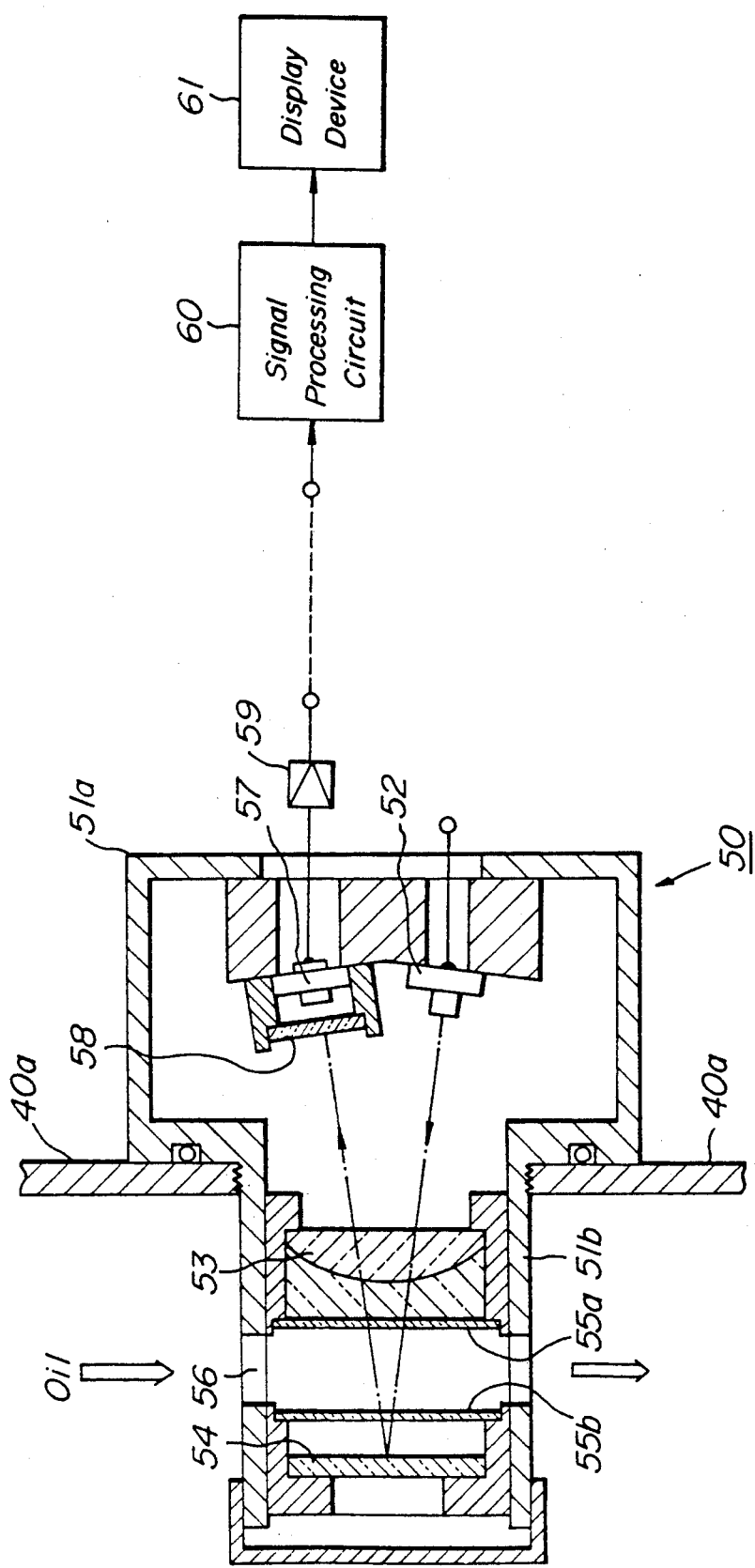
FIG._7b

APPARATUS FOR DETECTING DETERIORATION OF ENGINE OIL

BACKGROUND OF THE INVENTION

Field of the Invention and Related Art Statement

The present invention relates to a technique for detecting or measuring the condition of an engine oil, and more particularly to an apparatus for detecting the deterioration of the engine oil in an accurate and reliable manner. The present invention also relates to an apparatus for detecting the progress in the deterioration of the engine oil used in a motor car, while the apparatus is installed on the motor car.

Nowadays, the engine for the motor car has been developed to have high output power and excellent property, and thus the engine oil is liable to be used under severe conditions. Therefore, the deterioration of the engine oil has to be detected accurately and deteriorated engine oil has to be replaced with a new oil at a suitable time. To this end, the progress in the deterioration of the engine oil has to be detected accurately and undesired conditions such as the production of a large amount of sludges and the abrupt increase in the viscosity called oil thickening have to be avoided.

In general, the deterioration of the engine oil has been checked at a gas station in such a manner that an oil level gauge is pulled out of the engine and the dirtiness or blackening of a small amount of the engine oil adhered to a tip of the oil level gauge is visually checked and the viscosity of the engine oil is checked by fingers. However, such a known checking method is dependent on the experience of the human being, so that the degree of the deterioration of the engine oil could not be checked precisely. Particularly, the error due to the variation of respective operators could not be avoided.

In the Japanese Patent Application Laid-open Publication Kokai Sho 61-76938, there is described a known apparatus for detecting the deterioration of the engine oil. This known apparatus is based on the fact that the deterioration of the engine oil is related to the dirtiness of the engine oil. In this known apparatus, the engine oil whose dirtiness is to be detected is filled in a transparent vessel, a light beam having the visible wavelength is made incident upon the vessel, and the intensity of light transmitted through the vessel is detected to measure the dirtiness of the engine oil.

The above mentioned known apparatus can provide a measure for indicating the deterioration of the engine oil, because an amount of soots or carbon blacks and metal dusts introduced into the engine oil is increased in proportion to the time period during which the engine oil has been used. However, the inventors have found that the deterioration of the engine oil is not directly related to its dirtiness, but is mainly determined by the oxidation of the oil. Therefore, the known apparatus could not detect the true deterioration of the engine oil accurately, so that the engine oil could not be replaced at a suitable time on the basis of the detection result derived from the known apparatus.

The inventors have conducted various experiments and analyses and have found that the true deterioration of the engine oil is caused by the oxidation and the production of polymers due to the high operating temperature, so that the dirtiness could not indicate precisely the deterioration of the engine oil. For instance, although an amount of the soots and metal dusts introduced into the engine oil is small, the engine oil might be often deteriorated to a great extent due to the abrupt increase in the nitro oxidation under the high operating temperature. In such a case, there might be induced serious engine trouble by merely detecting the dirtiness of the engine oil. In this manner, the actual deterioration of the engine oil could not be measured only by detecting the dirtiness of the oil. The actual deterioration of the engine oil could be measured in the terms of total acid value, total base value, viscosity, etc. which is defined in ASTM. However, it is practically impossible to measure these parameters in a simple and reliable manner at the gas stations.

Furthermore, the above described known apparatus for detecting the dirtiness of the engine oil is constructed as a portable one and a small amount of the oil has to be sampled from the engine and is introduced into the apparatus. On the other hand, it is very convenient for drivers to indicate the deterioration of the engine oil during the actual running, so that the timing of replacing the engine oil could be determined correctly. Then, the engine oil could be exchanged at a suitable time, so that the running cost could be decreased, while the occurrence of the engine trouble due to the deterioration of the engine oil could be avoided.

SUMMARY OF THE INVENTION

The present invention has for its object to provide a novel and useful apparatus for detecting the true deterioration of the engine oil in an accurate and simple manner.

It is another object of the invention to provide an apparatus for detecting the deterioration of the engine oil without taking the oil out of the engine of the motor car and the progress in the deterioration of the engine oil can be continuously monitored, so that the driver can know the condition of the oil easily.

According to the invention, an apparatus for detecting the deterioration of an engine oil comprises:

light source means for projecting an infrared light beam upon the engine oil whose deterioration is to be detected;

photodetecting means for receiving infrared light transmitted through said engine oil to generate a photoelectrically converted output signal, a center wavelength of said infrared light received by the photodetecting means being set substantially to an infrared absorption peak wavelength of ester of nitric acid contained in the engine oil; and signal processing means for receiving said output signal from the photodetecting means to derive a signal representing the deterioration of the engine oil.

In a preferred embodiment of the apparatus according to the invention, a small amount of the engine oil whose deterioration is to be detected is sampled from the engine and is introduced into a measuring vessel.

The present invention also relates to a measuring vessel for use in the above mentioned apparatus for detecting the deterioration of the engine oil.

According to the invention, a measuring vessel for use in the apparatus for detecting the deterioration of an engine oil comprises a first plate, a second plate which is arranged in parallel with said first plate, and a spacer plate which is arranged between the first and second plates and having a recess which defines an oil retaining space together with the first and second plates. In a preferred embodiment of the measuring vessel according to the invention, the height of said first plate is larger than that of the second plate and spacer plate. Then, the first plate can serve as a guide for introducing the engine oil into the vessel. Further, it is advantageous that said recess is formed substantially in the U-shaped which is expanded toward the upper edge thereof. Then, air bubbles are hardly introduced and retained in the sampled engine oil. The measuring vessel is preferably made of hard type polyvinyl chloride resin, polymethylpentene resin, polypropylene resin or any other synthetic resin whose transmissivity for the infrared light is very small, so that the infrared light is hardly absorbed by the vessel and the measurement can be carried out precisely.

The inventors of the present application have recognized the following fact and have achieved the present invention on the basis of this recognition. The causes of the deterioration of the engine oil can be roughly classified as follows.

(1) the oxidation of the oil due to the lack or loss of the anti-oxidation agent;

(2) the decrease in various properties due to the consumption of the addition agents:

(3) the introduction of undesired substances such as fuel, combustion products and dusts:

The above mentioned causes are sometimes produced independently from each other, but in general, the engine oil is deteriorated by a complicated combination thereof. The inventors have confirmed that among these causes the oxidizing deterioration has to be mainly considered. For the oxidizing deterioration, the action of the nitrides $NO_x$ contained in exhaust gas discharged from the gasoline engine, gas engine, diesel engine, etc. has an intimate relation to the deterioration of the engine oil. In the oxidizing reaction under the condition of the high temperature, the nitrides $NO_x$ serves as a catalyst for the oxidizing reaction and the carbon hydrides RH are progressi·ely changed into nitro oxides to produce RONO and $RONO_2$ in the following manner.

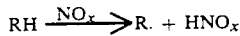

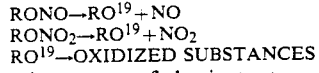

$RONO \rightarrow RO^{19} + NO$
$RONO_2 \rightarrow RO^{19} + NO_2$
$RO^{19} \rightarrow$ OXIDIZED SUBSTANCES The inventors of the instant application have found that an amount of ester of nitric acid $RONO_2$ contained in the engine oils has an intimate correlation with the total acid value, so that the deterioration of the engine oil can be detected accurately by measuring an amount of the ester of nitric acid contained in the engine oil.

According to the present invention, an amount of the ester of nitric acid is measured by detecting an amount of infrared light absorbed by the ester of nitric acid by using infrared light having the wavelength which is substantially equal to the infrared absorption peak wavelength of the ester of nitric acid. Then, by effecting the infrared light absorption measurement for the engine oil by using the infrared light whose wavelength is substantially equal to the infrared absorption peak of the ester of nitric acid, it is possible to obtain the photoelectric output signal representing an amount of the ester of nitric acid and the progress of the deterioration of the engine oil can be detected in a precise manner. As explained above, in the preferred embodiment of the apparatus according to the present invention, the measuring vessel is made of hard type polyvinyl chloride resin, polymethylpentene resin, and polypropylene resin. These materials have no specific absorption in the wavelength range including the infrared absorption peak of the ester of nitric acid, so that the absorption measurement is not affected by the vessel. Further, the above mentioned materials are cheap and thus the measuring vessel may be discarded without increasing the cost of the measurement. Particularly, the hard type polyvinyl chloride resin has a high mechanical strength, so that the thickness of the wall of the measuring vessel can be sufficiently small. This results in the increase in the sensitivity of measurement.

BRIEF DESCRIPTION OF THE DRAWINGS

FIGS. 2a and 2b are schematic cross sectional view and block diagram illustrating an embodiment of the portable type engine oil deterioration detecting apparatus according to the invention;

FIGS. 4a to 4c are perspective views depicting the method of manufacturing the measuring vessels;

FIG. 5 is a graph representing the relation between the absorption and the thickness of the material of measuring vessel;

FIGS. 6a and 6b are graphs showing the relation between the output from the apparatus according to the invention and the total acid value of the gasoline engine oil and gas engine oil respectively, and then FIG. 6c is a graph representing the relation between the output signal from the known apparatus and the total acid value;

FIGS. 7a and 7b, show an embodiment of the oil deterioration detecting apparatus according to the invention which is installed in the engine of the car;

DESCRIPTION OF THE PREFERRED EMBODIMENTS

Figure 1:
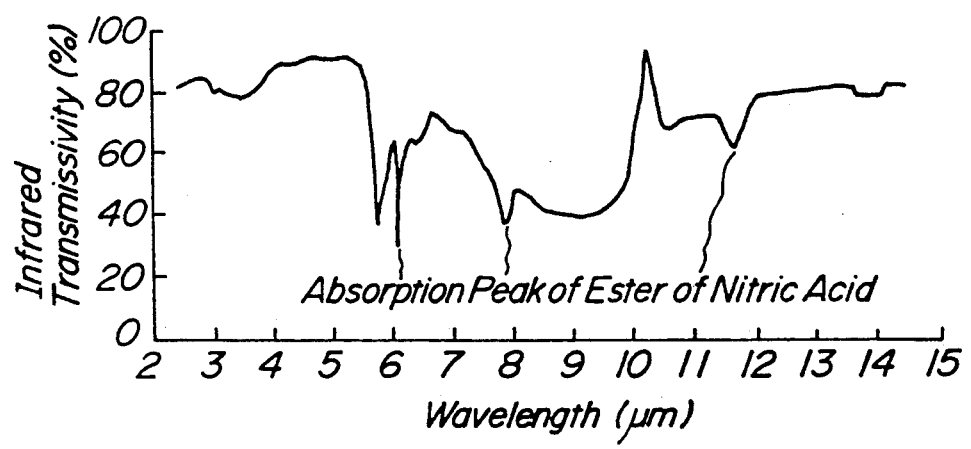
FIG. 1 is a graph showing the infrared absorption spectrum characteristic of the deteriorated engine oil.

FIG. 1 is a graph showing the infrared absorption spectrum characteristic of a deteriorated engine oil which has been used in an engine under a high way running test. The horizontal axis represents the wavelength of the infrared light and the vertical axis denotes the transmissivity of engine oil for the infrared light. As illustrated in FIG. 1, there are three infrared absorption peaks within a range from 2 micron meters to 15 micron meters. It has been confirmed that these three infrared absorption peaks are inherent to the ester of nitric acid. Therefore, when the absorption of the engine oil is measured by utilizing the infrared light including one of the three infrared absorption peaks, it is possible to measure an amount of the ester of nitric acid contained in the engine oil in a highly sensitive and accurate manner without being affected by other substances than the ester of nitric acid. Particularly, the deteriorated engine oil shows an abrupt absorption peak within a range near 6.1 micron meters, and thus it is possible to measure an amount of the ester of nitric acid contained in the engine oil in a very precise manner by using the infrared light beam whose center wavelength is equal to 6.1 micron meters.

Now an embodiment of the apparatus for detecting the deterioration of the engine oil according to the invention will be explained. In the present embodiment, the apparatus is constructed as a portable type one. FIG. 2a is a schematic cross sectional view showing the whole construction of the apparatus and FIG. 2b is a circuit diagram illustrating the construction of signal processing and driving circuits. The apparatus comprises a base 1 on which various optical elements are arranged. A light source 2 is secured to the base 1. In this embodiment, the light source 2 is formed by a ceramic heater which generates infrared light including the wavelength of 6.1 micron meters. The infrared light emitted from the light source 3 is chopped by a chopper 2 which includes a rotating disc 3a having a plurality of recesses formed along the periphery thereof and a motor 3b for rotating the disc. The chopped infrared light emanating from the chopper 3 is collected by a lens 4 and is made incident upon a measuring vessel 6 which contains an engine oil whose deterioration has to be detected. In the present embodiment, the measuring vessel 6 is made of hard type polyvinyl chloride resin. The measuring vessel 6 is supported by a supporting member 7 which is secured to the base 1. That is to say, the measuring vessel 6 having the engine oil 5 contained therein is inserted into a recess formed in the supporting member 7. The measuring vessel 6 made of the hard type polyvinyl chloride resin does not absorb the infrared having the wavelength substantially equal to the infrared absorption peak of the ester of nitric acid and therefore the measuring accuracy can be increased. Moreover, the cheap measuring vessel 6 is readily available at the measuring site, and thus the vessel may be discarded after the measurement. The infrared light beam being made incident upon the vessel 6 is absorbed by ester of nitric acid contained in the sampled engine oil. The infrared light emanating from the vessel 6 is received by a photodetector 9 by means of a filter 8 which is formed by a band pass filter having a center wavelength which is substantially equal to the infrared absorption peak of 6.1 micron meters of the ester of nitric acid, so that the infrared light having the wavelength of 6.1 micron meters is made incident upon the photodetector 9. In this manner, it is possible to detect the infrared light which has been subjected to the absorption due to the ester of nitric acid contained in the engine oil and the photodetector 9 produces a photoelectric output signal which represents an amount of the ester of nitric acid contained in the engine oil. The output signal of the photodetector 9 is amplified by an amplifier 10 and then is supplied to a signal processing circuit 11. In the signal processing circuit 11, the received signal is synchronously detected in accordance with a synchronizing signal which is also supplied to a driving circuit 12 for driving the chopper 3. In the signal processing circuit 11 there are stored various kinds of calibrating data such as zero data value and calibration curve data, and correction data for the optical system. By using the above mentioned data, the input signal is processed to derive an amount of the ester of nitric acid, and the value of the thus measured amount of the ester of nitric acid is displayed on a display device 13. This display may be digital display or analogue display. The signal processing circuit 11 and driving circuit 12 are provided on a printed circuit board which is arranged in a space between the base 1 and a housing 20. In this manner there can be obtained a portable type oil deterioration detecting apparatus which can be handled easily at the gas station to measure the true deterioration of the engine oil in a precise and reliable manner.

Now the measuring vessel 6 will be explained more in detail.

Figure 3A:
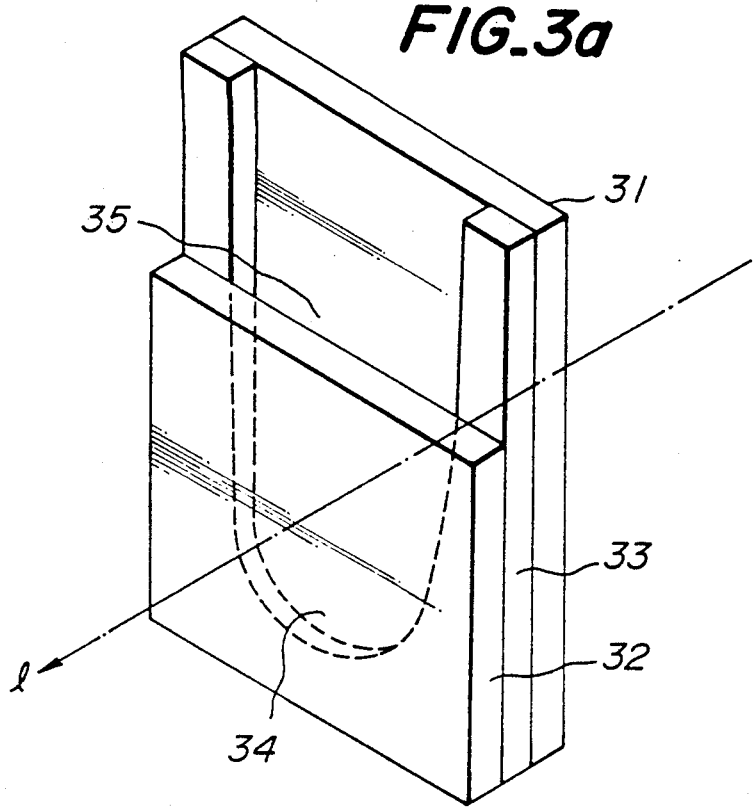
FIGS. 3a to 3c show the measuring vessel according to the invention for use in the apparatus shown in FIG. 2.
Figure 3B:
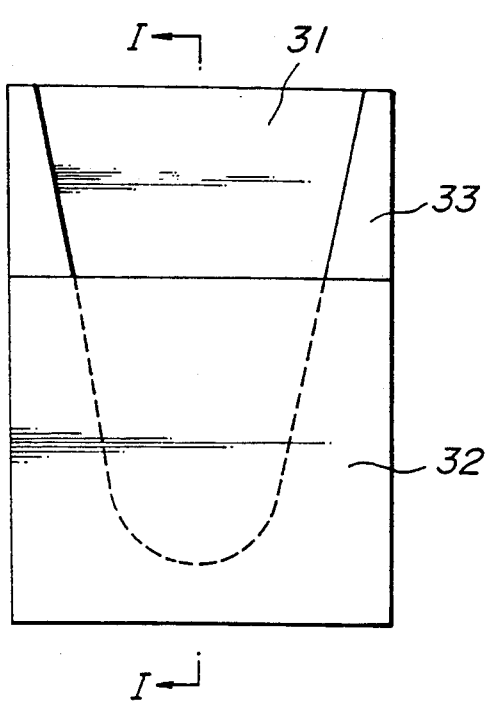
Figure 3C:
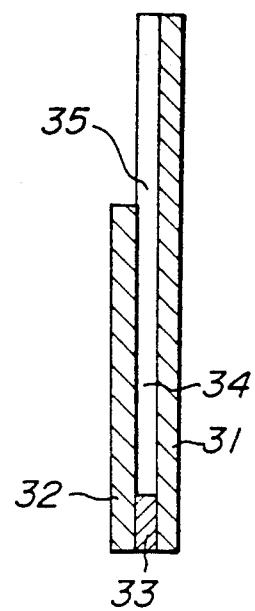

FIG. 3a is a perspective view of the vessel, FIG. 3b is a front view, and FIG. 3c is cross sectional view cut along a line I—I in FIG. 3b. Between a front plate 31 serving as an incident window and a rear plate 32 operating as an exit window is arranged a spacer plate 33, these plates being connected to each other by means of an adhesive agent to form a sample retaining space 34. In the spacer 33 there is formed a substantially U-shaped recess. It should be noted that the recess is gradually expanded outwardly toward the upper edge thereof. The thickness of the sample retaining space 34 is determined by the thickness of the spacer plate 33, so that it should be determined by considering an amount of infrared light absorbed by the sample. It has been experimentally found that the thickness of the spacer plate 33 is preferably set to 0.1~2.0 mm. By assembling the three plate-like members 31, 32 and 33 with the aid of a suitable adhesive agent, it is possible to attain the sample retaining space 34 which has the uniform thickness viewed in a direction perpendicular to the optical axis 1 and is expanded outwardly toward an opening 35. It should be noted that the sample retaining space 34 has no edge-like portion or projection, so that air bubbles are hardly introduced in the sample oil when the example oil is introduced into the space, and further air bubbles which might be introduced in the oil are liable to move upward and are disappeared rapidly. This enhances the accuracy and reliability of the measurement. In the present embodiment, the front plate 31 and the sides of the spacer plate 33 are extended above the opening 35, so that they functions to guide the engine oil. This is particularly advantageous for a thin measuring vessel.

FIGS. 4a to 4c show successive steps of a method of manufacturing the measuring vessel. In the present embodiment, a plurality of vessels are simultaneously formed in an economical manner. An elongated spacer plate 33a having a plurality of substantially U-shaped recesses are arranged between an elongated first plate 31a and an elongated second plate 32a as shown in FIG. 4a. Then, these plates 31a, 32a and 33a are cemented to each other by an adhesive agent to form an assembly depicted in FIG. 4b. Next the assembly is cut along lines S to form a plurality of measuring vessels illustrated in FIG. 4c. It is preferable to make the spacer plate 33a of a non-transparent or colored material. When the spacer plate 33a is made of the colored material, it is easy to visually find the sample retaining space and the operation of introducing the sample oil into the sample retaining space becomes easy. Further the assembling operation becomes easy when the spacer plate 33a is formed by a plate having adhesive layers applied on both sides thereof.

Now the material of the measuring vessel will be explained. First of all, the material of the measuring vessel has t be selected by considering the infrared absorption characteristics. FIG. 5 is a graph showing the transmissivity of various synthetic materials. The horizontal axis denotes the thickness of the synthetic resin materials, and the vertical axis represents the transmissivity at the wavelength of 6.1 micron meters. As shown in FIG. 5, polycarbonate resin has a strong absorption for the infrared light having the wavelength of 6.1 micron meters and the transmissivity becomes almost zero at the thickness of 0.5 mm. To the contrary, rigid polyvinyl chloride resin, polymethylpentene resin and polypropylene resin have the good transparency for the infrared light of 6.1 micron meters. For instance, at the thickness of 0.2 mm, the transmissivity becomes about 70%. Therefore, the measuring vessel is preferably made of rigid polyvinyl chloride, polypropylene and polymethylpentene resins. It should be noted that these synthetic resin materials might contain additions such as plasticizer. If the plasticizer absorbs the infrared light having the wavelength of about 6.1 micron meters, the measuring light is absorbed by the measuring vessel, so that the accuracy of the measurement becomes worse. Therefore, according to the present invention, the measuring vessel has to be made of the synthetic resin having no additions which absorb the measuring infrared light. Further, as can be understood from the graph shown in FIG. 5, when the measuring vessel has a large thickness, an amount of the measuring infrared light absorbed by the vessel becomes large, so that the thickness of the measuring vessel should be made as small as possible. However, when the thickness of the measuring vessel is made small, the mechanical strength of the vessel becomes decreased. Therefore, the measuring vessel is preferably made of the material having a small absorption for the infrared light as well as a high mechanical strength. Particularly, the rigid polyvinyl chloride resin has an elastic constant for bending of 28000 to 42000/cm$^2$ and is very suitable as the material of the measuring vessel.

Next some experimental results obtained by the apparatus according to the present invention will be explained.

FIGS. 6a and 6b show the results of the measurement obtained by detecting the deterioration of the engine oils used in gasoline engine and gas engine, respectively, with the aid of the apparatus according to the present invention and FIG. 6c illustrates a measured result obtained by the known apparatus. In these graphs, the horizontal axis denotes the total acid value in mgKOH/g and the vertical axis represents the output of the signal processing circuit in an arbitrary unit. In case of using the apparatus according to the invention, the output signal is increased in proportion to the increase in an amount of the total acid value. That is to say, the curves shown in FIGS. 6a and 6b express that there is a correlation between the total acid value and an amount of the ester of nitric acid. As shown in FIG. 6c, the output signal of the known apparatus has no relation with respect to the total acid value, so that the true deterioration of the engine oil could not be detected accurately. In the apparatus according to the present invention, an amount of the ester of nitric acid can be measured accurately and this amount of the ester of nitric acid is related to the total acid value which is directly related to the deterioration of the engine oil.

Now it is assumed that the threshold value of the total acid value is set to 3 mgKOH/g. Then, when the output of the apparatus exceeds a value of about 55, it can be determined that the engine oil has been deteriorated and thus has to be exchanged. In the known apparatus, although the output of the apparatus is in the dangerous zone, i.e. in the red range of 8 to 12, the total acid value of some engine oils is smaller than 3 mgKOH/g and should not be replaced with a new engine oil.

In the above mentioned experimental results, the deterioration of the engine oil is detected by using the infrared of 6.1 micron meters which is equal to the specific infrared absorption peak of the ester of nitric acid, however according to the invention, the accuracy of the measurement can be further improved by using both the infrared of the wavelength which is absorbed by the ester of nitric acid and an infrared having a wavelength outside the absorption range of the ester of nitric acid. In the used engine oil, there are contained various kinds of impurities such as soots and metal powders which absorb or reflect the measuring infrared light having the wavelength of 6.1 micron meters, and thus these impurities might decrease the output signal. The inventors have found that the decrease in the amplitude of the output signal due to these impurities appears over the whole wavelength range, so that the dirtiness of the engine oil due to these impurities might be introduced in the measured result obtained by using the infrared light having the wavelength of 6.1 micron meters as a noise to a small extent. The sampled engine oil is measured by using an infrared light having a wavelength which does not include the infrared absorption peak of the ester of nitric acid, for instance 4 to 5 micron meters to detect the absorption of the infrared light due to the impurities other than the ester of nitric acid. Then, the thus detected absorption value is subtracted from the measurement value obtained by using the infrared of the wavelength substantially equal to the absorption peak of the ester of nitric acid. In this manner, an amount of the ester of nitric acid can be detected accurately without being affected by the impurities. In this case, the measurement is carried out by alternately inserting into the optical axis the band pass filter having the transmission wavelength of 6.1 micron meters and a band pass filter having the transmission wavelength range of 4 to 5 micron meters. The output signals are processed in the signal processing circuit to derive the signal representing the deterioration of the engine oil.

Now another embodiment of the apparatus according to the invention will be explained with reference to FIGS. 7a and 7b. In the present embodiment, the apparatus is installed on a motor car. FIG. 7a shows the position on the engine at which the engine oil deterioration detecting apparatus according to the invention is provided, and FIG. 7b is a cross sectional view illustrating the construction of the apparatus. In the present embodiment, the apparatus is arranged on the oil pan of the engine and the output signal derived from the apparatus is supplied to an indicator provided on a front panel of the car, so that the driver can always know the progress of the deterioration of the engine oil without sampling the engine oil. The engine comprises oil pan 40, cylinder block 41, cylinder head 42, head cover 43 and air cleaner 44. In the side wall of the oil pan is formed a through hole and the apparatus 50 is secured to the oil pan through this hole. The apparatus comprises housing 51 in which various kinds of optical systems are arranged. The housing 51 includes a base portion 51a and a projection 51b. The projection 51b is protruded into the side wall of the oil pan 40a and is secured to the side wall by means of an O ring. Within the base portion 51b is arranged a light source 52 emitting infrared light including the wavelength of 6.1 micron meters. The infrared light is collected by a lens 53 and is made incident upon a reflection mirror 54 via two transparent plates 55a and 55b which are separated from each other by a predetermined distance and are made in parallel with each other. In a portion of the projection 51b situating between the plates 55a and 55b is formed a passage 56 through which the engine oil flows. The two transparent plates 55a and 55b are made of rigid polyvinyl chloride and are secured to the projection 51b in a liquid-tight manner, so that the engine oil does not leak out of the apparatus. The infrared light collected by the lens 53 is absorbed by the engine oil passing through the passage 56 and is reflected by the mirror 54. Then, the infrared light is absorbed again by the engine oil and is made incident upon a photodetector 57 via the lens 53. In front of the photodetector 57 is arranged a band pass filter 58 which transmits infrared light having the wavelength of 6.1 micron meters which is equal to the infrared absorption peak of the ester of nitric acid contained in the engine oil. Therefore, the photodetector 57 produces an output signal which is proportional to an amount of the ester of nitric acid in the engine oil. The output signal generated by the photodetector 57 is amplified by an amplifier 59 and is then supplied to a signal processing circuit 60. The signal processing circuit 60 processes the input signal and produces an output which represents the deterioration of the engine oil. This output signal from the signal processing circuit 60 is further supplied to a display device 61 which is arranged on the front panel of the car. In the display device 61, the deterioration of the engine oil is displayed as the analogue or digital mode. Alternately, the detected deterioration is compared with a predetermined threshold value and when the deterioration exceeds the threshold value, an alarm may be displayed. In this manner, the driver of the car can directly know the deterioration of the engine oil and thus the engine oil can be replaced at a suitable time and any trouble due to the deterioration of the engine oil can be positively avoided. It should be noted that the transparent plates 55a and 55b may be removed and the passage 56 through which the engine oil passes may be defined by the lens 53 and reflection mirror 54. Then, the construction of the apparatus becomes simple.

Figure 8:
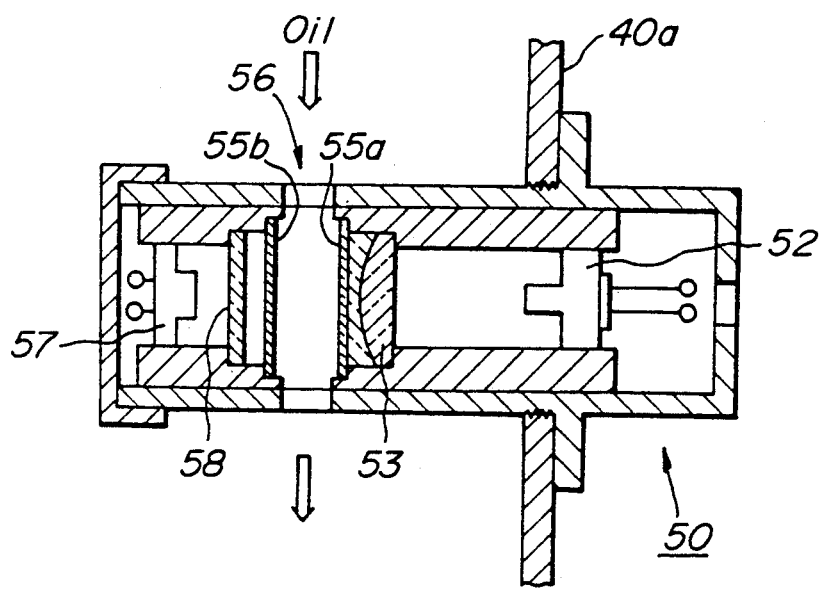
FIG. 8 is a cross sectional view illustrating a modification of the embodiment shown in FIG. 7.

FIG. 8 is a cross section showing the construction of another embodiment of the apparatus according to the present invention. In the present embodiment, portions similar to those shown in FIG. 7 are denoted by the same reference numerals used in FIG. 7. The infrared light emitted from the light source 52 and collected by the lens 53 is made incident upon the engine oil passing through the passage 56 defined by the transparent plates 55a and 55b. The infrared light transmitted through the engine oil is made incident upon the photodetector 58 via the band pass filter 57 having the center wavelength of 6.1 micron meters. In the present embodiment, since the measuring infrared light is transmitted through the engine oil only once, it is possible to make wider the width of the passage through which the engine oil passes.

Figure 9:
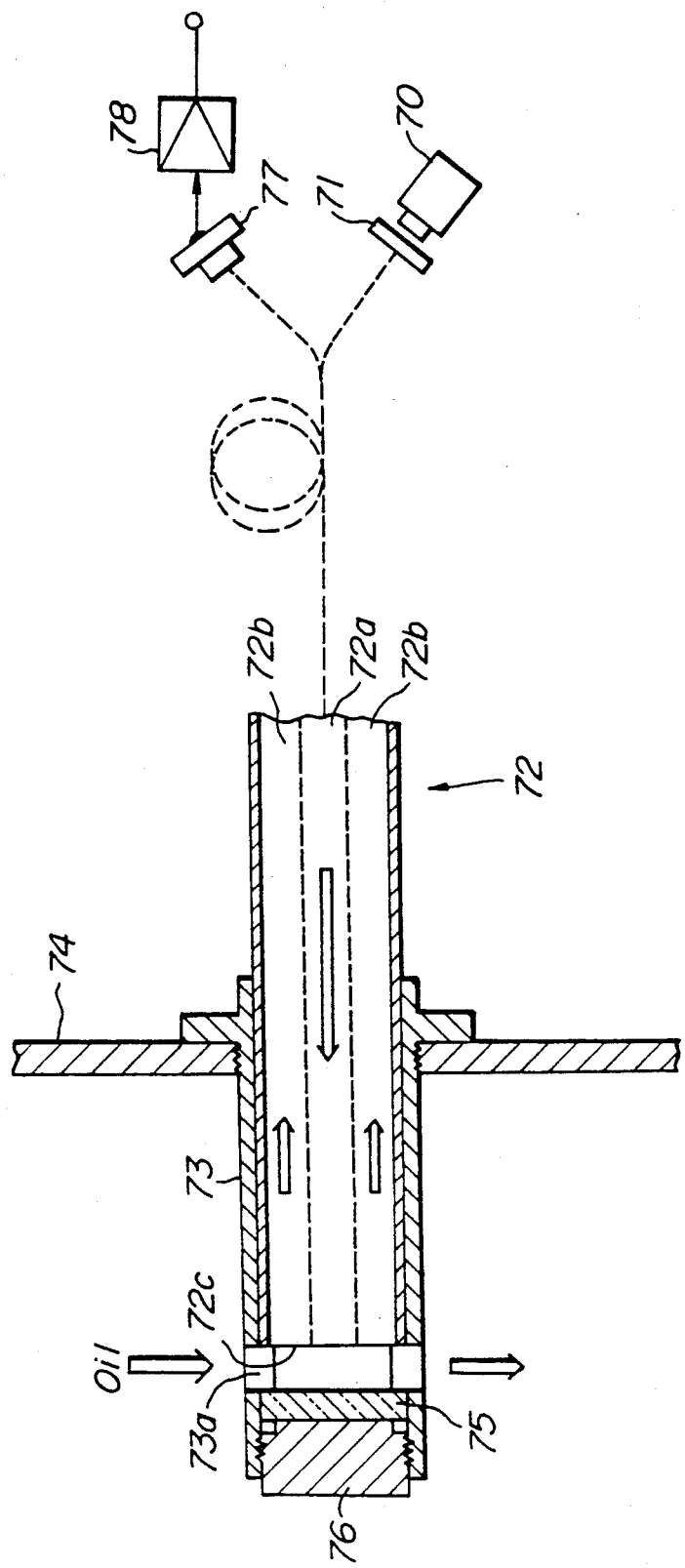
FIG. 9 is a cross sectional view depicting another embodiment of the apparatus according to the invention.

FIG. 9 is a schematic cross sectional view showing still another embodiment of the apparatus according to the invention. In the present embodiment, the light source and photodetector may be arranged at any desired positions by using an optical fiber. That is to say, a double light transmitting fiber having a central light transmitting portion and a peripheral light transmitting portion is utilized. Infrared light emitted by a light source 70 is made incident upon an incident end of a center transmitting portion 72a of an optical fiber 72 by means of a filter 71 having a center transmission wavelength of 6.1 micron meters. The optical fiber 72 is made of quartz which has no specific absorption at a wavelength range including 6.1 micron meters. The other end of the optical fiber 72 is secured to a casing 73 which is fixed to an oil pan 74. At a front end of the casing 73 is secured a reflection mirror 75 by means of an end cap 76. Between the reflection mirror 75 and the end face 72c of the optical fiber 72 is formed a passage 73a through which the engine oil is passed. The infrared light transmitted through the center transmitting portion 72a of the optical fiber 72 is made incident upon the engine oil flowing through the passage 73a and is absorbed by the ester of nitric acid contained in the engine oil. The infrared light transmitted through the engine oil is reflected by the mirror 75 and is made incident upon the peripheral transmitting portion 72b of the optical fiber. The infrared light transmitted through the optical fiber 72 is made incident upon a photodetector 77. Then, the photodetector 77 produces an output signal which represents an amount of the ester of nitric acid contained in the engine oil. As explained above, in the present embodiment, the light source and the photodetector may be arranged at any desired positions, so that they are not affected by the temperature and vibration. Further the freedom in designing the apparatus is increased.

Figure 10:
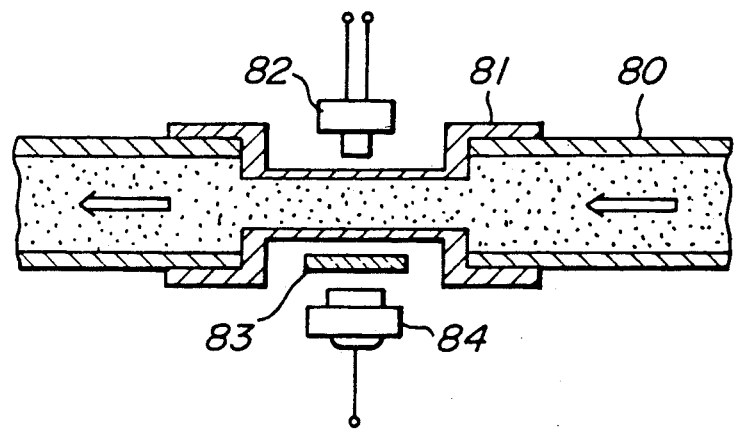
FIG. 10 is a cross sectional view showing another embodiment of the apparatus according to the invention.

FIG. 10 shows another embodiment of the apparatus according to the invention. In the present embodiment, the apparatus is arranged at a portion of an engine oil supplying pipe. In an engine oil supplying pipe 80 is inserted a transparent tube-like member 81 made of rigid polyvinyl chloride resin, and a light source 82 and a photodetector 83 are arranged on respective sides of the member 81. Infrared light emitted by the light source 82 is made incident upon the engine oil passing through the tube-like member 81 and infrared light transmitted through the tube-like member is made incident upon the photodetector 84 via a band pass filter 83 which transmits the infrared light having the wavelength of 6.1 micron meters. In the present embodiment, the apparatus can be easily installed in the existing engine, so that the construction becomes very simple.

Figure 11:
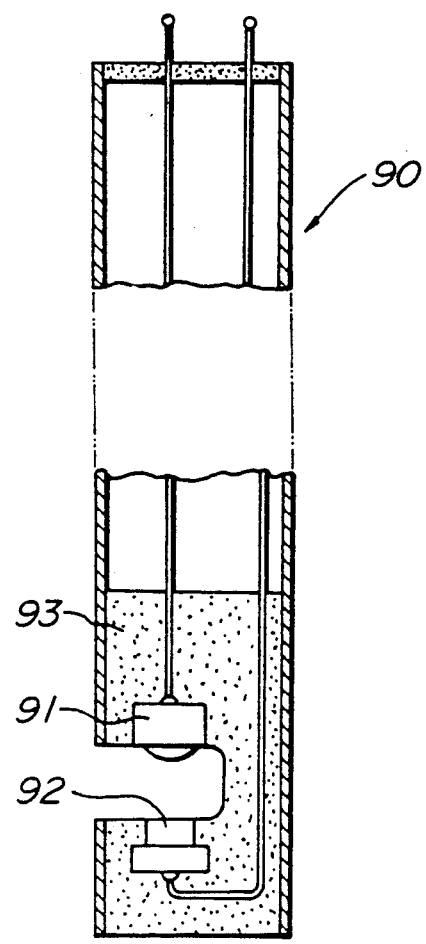
FIG. 11 is a cross sectional view illustrating still another embodiment of the apparatus according to the invention which is constructed in the form of the oil level gauge.

FIG. 11 is a cross sectional view illustrating still another embodiment of the apparatus according to the invention. In the present embodiment, the apparatus is constructed like as the oil level gauge which is inserted in a tube communicated with the oil pan. An oil level gauge 90 comprises a light source 91 emitting infrared light having the wavelength of about 6.1 micron meters and photodetector 92 which receives infrared light transmitted through the engine oil. These elements are arranged in a distal end of the oil level gauge 90 and are embedded in a fitting agent 93. In the present embodiment, the deterioration of the engine oil can be detected without sampling the engine oil out of the engine, because the deterioration of the engine oil can be measured only by inserting the oil level gauge to such an extent that the distal end of the gauge is immersed in the engine oil contained in the oil pan.

As explained above in detail, according to the present invention the true deterioration of the engine oil can be detected in an accurate manner by measuring an amount of the ester of nitric acid contained in the deteriorated engine oil on the basis of the fact that the deterioration of the engine oil is substantially proportional to an amount of the ester of nitric acid contained in the engine oil. Particularly, when the optical path in the engine oil is made short, the apparatus can be made small and can be formed as the portable type one. Therefore, the deterioration of the engine oil can be detected easily at the gas station.

Moreover, when the detected deterioration of the engine oil is displayed on the front panel of the car, the driver can know the progress in the deterioration of the engine oil, so that the engine oil can be replaced at a suitable timing and any trouble due to the deterioration of the engine oil can be effectively avoided.

What is claimed is:

1. An apparatus for detecting the deterioration of an engine oil comprising:
   light source means for projecting an infrared light beam upon the engine oil whose deterioration is to be detected;
   photodetecting means for receiving infrared light transmitted through said engine oil to generate a photoelectrically converted output signal, a center wavelength of said infrared light received by the light detecting means being set substantially to an infrared absorption peak wavelength of ester of nitric acid contained in the engine oil; and
   signal processing means for receiving said output signal from the photodetecting means to derive a signal representing the deterioration of the engine oil.

2. An apparatus according to claim 1, wherein said light source means comprises a light source which emits infrared light having a center wavelength of about 6.1 micron meters, and said photodetecting means comprises a photodetector and a band pass filter having a center wavelength of 6.1 micron meters.

3. An apparatus according to claim 2, wherein said light source comprises a ceramic heater.

4. An apparatus according to claim 1, further comprising a measuring vessel in which said engine oil is received, whereby said infrared light is made incident upon the measuring vessel and the infrared light transmitted through the measuring vessel is made incident upon the photodetecting means.

5. An apparatus according to claim 4, wherein said measuring vessel is made of a material selected from a group consisting of rigid polyvinyl chloride resin, polymethylpentene resin and polypropylene resin.

6. An apparatus according to claim 5, wherein said measuring vessel comprises a flat plate, a second plate which is arranged in parallel with said first plate, and a spacer plate which is arranged between the first and second plates and having a recess which defines a oil retaining space together with the first and second plates.

7. An apparatus according to claim 6, wherein the height of said first plate is larger than that of the second plate.

8. An apparatus according to claim 7, wherein said recess is formed substantially in a U-shape.

9. An apparatus according to claim 8, wherein said recess formed in the spacer plate is expanded outwardly toward the upper edge thereof.

10. An apparatus according to claim 1, further comprising a display means for receiving said signal supplied from said signal processing means and displaying a signal representing the deterioration of the engine oil.

11. A car including an apparatus for detecting the deterioration of an engine oil, said apparatus comprising:
    light source means for projecting an infrared light beam upon the engine oil whose deterioration is to be detected;
    photodetecting means for receiving infrared light transmitted through said engine oil to generate a photoelectrically converted output signal, a center wavelength of said infrared light received by the light detecting means being set substantially to an infrared absorption peak wavelength of ester of nitric acid contained in said engine oil;
    signal processing means for receiving said output signal from said photodetecting means to derive a signal representing the deterioration of said engine oil; and
    a display means for receiving said signal supplied from said signal processing means and displaying a signal representing the deterioration of said engine oil,
    wherein said display means is provided on a front panel of said car, said car having an engine for which said engine oil is used.

12. A car according to claim 11, further comprising a housing having a base portion which is arranged outside an oil pan of the engine and a projection which is arranged inside the oil pan, whereby said light source means and photodetecting means are arranged in said housing, and said projection includes a passage through which the engine oil is to be passed.

13. A car according to claim 12, wherein said light source means and photodetecting means are arranged in said base portion of the housing, a reflection mirror is arranged in said projection at such a position which is opposite to said light source means and photodetecting means with respect to said passage.

14. A car according to claim 13, wherein said passage is defined by a pair of plates which are transparent to the infrared light.

15. A car according to claim 12, wherein said passage is defined by a lens for collecting the infrared light and the reflecting mirror.

16. A car according to claim 12, wherein said light source means is arranged on one side of said passage and said photodetecting means is arranged on the opposite side of said passage.

17. A car according to claim 11, further comprising a casing which is inserted into an oil pan of the engine, an optical fiber for transmitting the infrared light emitted from said light source means into said casing, a passage formed in said casing, through said passage the engine oil being passed, a reflection mirror arranged in said casing for reflecting the infrared light transmitted through the engine oil toward the engine oil, and an optical fiber for transmitting the infrared light transmitted through the engine oil into the photodetecting means, whereby the infrared light is transmitted twice through the engine oil passing through said passage.

18. A car according to claim 11, further comprising a tube-like member through which the engine oil passes, said tube-like member being made of a material which does not absorb the infrared light, whereby said light source means and said photodetecting means are arranged on respective sides of said tube-like member.

19. A car according to claim 1, further comprising a rod-like member insertable into a tube which is communicated with an oil pan of an engine of a car and into which an oil level gauge is inserted, whereby said light source means and photodetecting means are arranged in a distal end of said rod-like member such that they are faced to each other via a space within which the engine oil is filled when the rod-like member is fully inserted into said tube.

* * * * *